United States Patent [19]

Warncke et al.

[11] 4,012,809
[45] Mar. 22, 1977

[54] METHOD AND APPARATUS FOR ATTACHING THE FREE END OF A WITHDRAWING TAPE TO A TAMPON ROLL

[75] Inventors: Niels Warncke, Metzkausen; Wolfgang Johst, Gevelsberg, both of Germany

[73] Assignee: Dr. Carl Hahn GmbH, Dusseldorf, Germany

[22] Filed: Apr. 25, 1975

[21] Appl. No.: 571,454

Related U.S. Application Data

[62] Division of Ser. No. 408,215, Oct. 19, 1973, Pat. No. 3,946,463.

[30] Foreign Application Priority Data

Oct. 30, 1972 Germany ............... 2253180

[52] U.S. Cl. ............................................. 19/144.5
[51] Int. Cl.² ........................................ A61L 15/00
[58] Field of Search .......... 19/144.5, 149; 128/270, 128/285, 263

[56] References Cited

UNITED STATES PATENTS

| | | |
|---|---|---|
| 2,584,913 | 2/1952 | Parish ................ 19/144.5 |
| 2,690,597 | 10/1954 | Greiner et al. ................ 19/144.5 |
| 3,852,847 | 12/1974 | Etz ................ 19/144.5 |
| 3,874,031 | 4/1975 | Simon ................ 19/144.5 |

*Primary Examiner*—Dorsey Newton
*Attorney, Agent, or Firm*—Jason Lipow

[57] ABSTRACT

An improvement in an apparatus for winding a batt of material in strip form carrying a free end of a withdrawal tape to form a rolled body thereof having withdrawal tape attached thereto which comprise a forked shaped totatable winding mandrel having fork tines, means for moving said winding mandrel back and forth in the plane of movement of said batt of material said fork tines positioned so as to straddle the longitudinal side of said batting material which carries the free end of the withdrawal tape with it, the improvement residing in that said winding mandrel contains an interior bore lengthwise thereof which bore is connected to a vacuum source means for transporting said batt of material in rolled form from said winding mandrel to a subsequent work station disposed on the side of the so-formed roll that carries the free end of the withdrawal tape.

5 Claims, 5 Drawing Figures

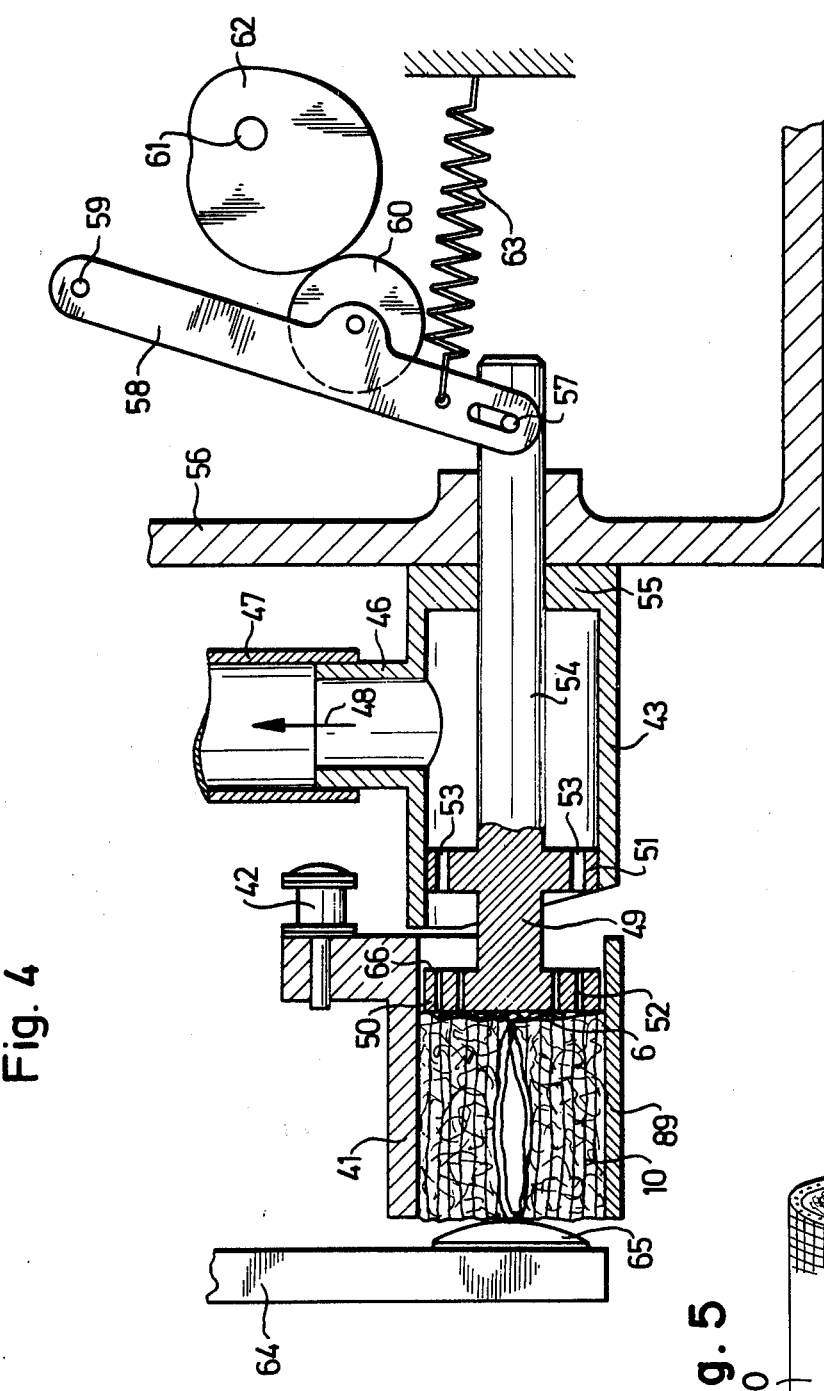
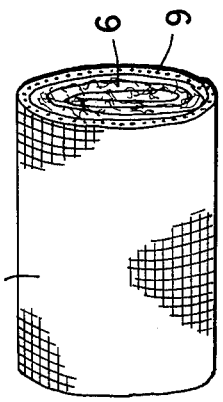

METHOD AND APPARATUS FOR ATTACHING THE FREE END OF A WITHDRAWING TAPE TO A TAMPON ROLL

This is a division, of application Ser. No. 408,215 filed Oct. 19, 1973, now U.S. Pat. No. 3,946,463.

BACKGROUND OF THE INVENTION

1. FIELD OF THE INVENTION

The invention concerns a method and apparatus for the attachment of the free end of a withdrawing tape joined to a strip of batting to one end of a tampon roll formed by rolling the strip of batting and constituting a semi-finished product for tampons serving especially for feminine hygiene.

2. DISCUSSION OF THE PRIOR ART

It is in the prior art through DT Pat. No. 915,382 to press the free end of a withdrawing tape spiral-wise during the production of the roll so that the free end of the withdrawing tape, which is joined to the batting strip, will remain adhering to the roll when the roll is transported from the rolling station to the pressing station and while the roll is being pressed to form the tampon. This application of the free end of the withdrawing tape to the roll in spiral form was reliable at the production rates commonly used hitherto and was therefore satisfactory.

OBJECTS OF THE INVENTION

The object of the invention is the creation of a method and an apparatus to assure that even at substantially higher production rates the free end of the withdrawing band of a tampon or similar article will be perfectly applied to one end of a roll and will adhere so tightly that it will remain securely in this position when the batting roll is then transported to the tampon pressing station and when the roll is thereafter pressed to form the tampon, and also when the tampon is wrapped and when the wrapping is removed, but will nevertheless be able to be detached from the tampon by the user prior to insertion, without the raising of nap.

SUMMARY OF THE INVENTION

The invention achieves this object by the fact that the free end of the withdrawing tape is placed in a position wherein it extends away from the batting strip before the batting strip is rolled and it is applied adheringly to the one end of the roll after the rolling process has been completed. In this manner, very high rolling speeds can be set up without having to pay heed to the free end of the withdrawing tape joined to the batting. This is because the position of the free end of the withdrawing tape extending away from the batting strip assures that the free end will remain completely unaffected by the winding process. It has been found that the application of the free end of the withdrawing tape to the end of the roll can be performed at very high production speeds if it is not done until after the rolling process has been completed.

It is recommended that the free end of the withdrawing tape be brought into a position extending coaxially with the roll axis before the batting strip is rolled. This creates more favorable conditions for the rolling of the batting strip, especially when, in accordance with a further development of the method, before the rolling of the batting strip begins, the free end of the withdrawing tape is aspirated into the position extending away from the batting strip.

The invention relates to an improvement in a process for preparing a tampon having a withdrawal string or tape spirally wound and positioned within a depressed cavity in the withdrawal end of the tampon, the improvement comprising forming the tampon body by winding a batting material strip to which is attached a withdrawal string or tape while maintaining said string or tape disposed away from said material strip and maintaining it coxial with respect to the roll axis of the batting material strip, disposing same in a recessed cavity disposed at the withdrawal end of the so formed tampon.

This invention also relates to an improvement in an apparatus for winding a batt of material in strip form carrying a free end of a withdrawal tape to form a rolled body thereof having said withdrawing tape attached thereto which comprise a forked shaped rotatable winding mandrel having fork lines, means for moving said winding mandrel back and forth in the plane of movement of said roll of materials, said fork lines positioned so as to straddle the longitudinal side of said batting material which carries the free end of the withdrawal tape with it, the improvement residing in that said winding mandrel contains an interior bore lengthwise thereof which bore is connected to a vacuum source, means for transporting said batt of material in rolled form from said winding mandrel to a subsequent work station disposed on the side of the so-formed roll that carries the free end of the withdrawal tape.

An advantageous further improvement is based upon pulling the withdrawing string or tape out of its holder as the roll is advanced to a withdrawing tape application station in which the withdrawing tape is aspirated into a cylinder and is then pressed in a random state against the end of the roll. The advantage of this procedure lies in the fact that no special measures need be taken to carry the withdrawing ribbon along from its extended position in the direction of the rolling station, while on the other hand the re-aspiration of the free end of the withdrawing tape in the area of the withdrawing tape application station can take place in the necessary short time, and furthermore, it offers the appreciable advantage that the free end is pressed in a random, i.e., jumbled, state against the end of the roll. It has been found that if the free end is in a random position it will adhere better to the end of the roll because the nunmber of points of contact between different lengths of the free end of the withdrawing tape and the tampon batting material of the roll is considerably increased and the contact between the withdrawing tape and the tampon batting material takes the form of slight intermeshing of the fibers of the withdrawing tape with those of the roll.

It is desirable to use for the practice of the above-described method an apparatus which is provided with a fork-shaped, rotatable winding mandrel which is movable back and forth in the plane of movement of a fiber batting strip, transversely of the latter, the fork tines of the winding mandrel straddling the longitudinal side of the batting strip which carries the free end of the withdrawing tape with it, the apparatus being characterized by the fact that the winding mandrel is bored through lengthwise and can be connected to a vacuum source, while the winding mandrel is followed, in the direction of transport of the roll, by a withdrawing tape application station which is disposed on the side of the roll that carries along the free end of the withdrawing tape.

To facilitate the aspiration of the free end of the withdrawing tape, the fork slot of the winding mandrel is cut deeper into the wall of the mandrel on one side in the direction away from the end of the fork. The result of this is that this deeper fork web is located at an axial distance from the opposite longitudinal side of the batting strip extending through the fork slot of the winding mandrel and thus forms a clear, exposed aperture for the aspiration of the free end of the withdrawing tape, which consequently is more effectively and rapidly aspirated into the hollow winding mandrel. Here, the free end of the withdrawing tape is in a position coaxial with the winding axis, in which the winding of the batting strip on itself takes place without regard for the free end of the withdrawing tape.

According to a desirable embodiment, a pinion is fastened on the winding mandrel to mesh with a gear on the shaft of an intermittent drive connected by a flexible drive member to a motor.

In a further development of this embodiment, a shaft is affixed to a cam engaging one end of a lever whose other end cooperates with a yoke which straddles the pinion and through which the winding mandrel passes in a freely rotatable manner, and which is displaceably carried upon a guide rod parallel to said mandrel.

The station for the application of the free end of the withdrawing tape consists of a cylindrical housing whose bore is located opposite and approximately coaxially with the rolls and receives a sliding piston consisting of two heads joined together in an axially spaced relationship, said heads being provided with apertures, and the cylinder being provided with a connection for a vacuum source.

The desired reliability of the aspiration of the free end of the withdrawing tape in the area of the withdrawing tape application station is increased considerably if the approximately perpendicular edge of the orifice of the cylinder facing the free end of the withdrawing tape is made to slant downwardly away from the roll. An aspiration opening is thereby created which is aimed in the direction of the free end of the withdrawing tape extending away from the end of the roll, so that the free end of the withdrawing tape can be rapidly and effectively aspirated into the cylinder.

It is furthermore recommencable that the one head of the sliding piston which faces the roll be provided with a plurality of through bores of small diameter, while the other head facing the floor of the cylinder contains bores of a larger diameter in comparison. The large bore in the piston head facing away from the roll permit its movement within the cylinder in the direction away from the roll, because the air between the piston head and the bottom of the cylinder can escape through the large bores and into the vacuum connection, while the small bores in the piston head facing the roll assure that the aspirated free end of the withdrawing tape will remain lying randomly on the end face of the other piston head.

Preferably, the clear axial distance between the two piston heads corresponds approximately to the inside diameter of the suction connection, which extends outwardly from approximately the longitudinal center of the cylinder.

A blocking means provided at the end of the roll that faces away from the cylinder housing serves to counter the pressure applied to the other end of the roll when the free end of the withdrawing tape is pressed against it.

It is advantageous to use an apparatus in which an upper and a lower endless flexible member can be driven stepwise in wynchronism, one clockwise and the other counter-clockwise in a common plane of rotation and is equipped with tension jaws and gripping jaws, a severing bail that can swing transversely to the batting, and with approximately semicircular winding cups mounted laterally on the associated endless flexible member, into which cups the plane of rotation and straddling the batting strip, a curved lever being articulated upon each winding cup of the lower flexible member so as to be able to pivot over the winding station is situated with is followed in the direction of rotation of the lower flexible member in the area of the cam by an ejector plunger which can plunge into the winding cups transversely of their direction of movement, the apparatus being characterized in that the cylinder housing of the withdrawing tape application station is disposed in each case coaxially with the winding cups in the area of the lower section of the lower flexible member and of the surface of the cam, and the surface of the cam extends approximately over the entire area in which the lower flexible member moves from its roll processing section to its bottom section, as well as along the bottom section beyond the roll ejection station formed by the ejector plunger, to a point beyond which the lower flexible member passes back into the roll processing section.

The pressing head of the sliding piston is preferably outside of the cylinder housing and in the winding cup at the end of its working stroke.

BRIEF DESCRIPTION OF DRAWING

In the drawing, there is shown diagrammatically, by way of example, an apparatus for the practice of the method of the invention. Referring to such drawings.

FIG. 4 represents the withdrawing tape application station of FIG. 3 in the pressing position, and FIG. 5 is a perspective view of a finished roll with the free end of the withdrawing tape pressed against the end thereof.

DESCRIPTION OF SPECIFIC EMBODIMENT

Figure 2:
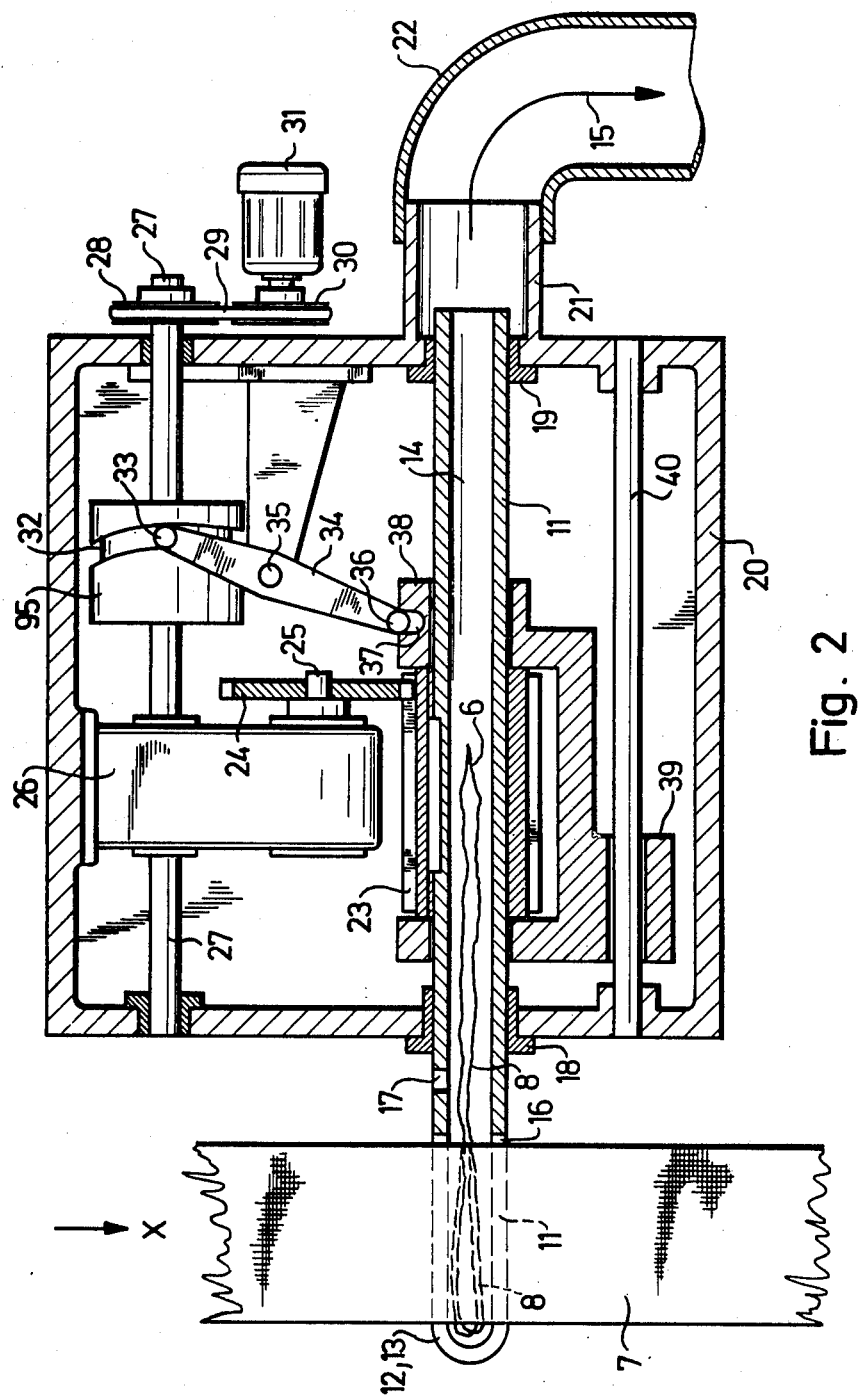
FIG. 2 shows a plan view of the rolling station of FIG. 1 on an an enlarged scale, along lines II—II.

In the drawings there is shown an apparatus for applying the free end 6 of a withdrawing tape 8 joined to a batting strip 7 to one end 9 of tampon roll 10 formed by rolling up the batting strip and serving as a semi-finished product for a tampon to be used especially in feminine hygiene. A rotatable, forked winding mandrel 11 shown in FIG. 2 is adapted for movement back and forth in the plane of movement of the fiber batting strip 7, transversely of the latter, the tines 12 and 13, of the fork of the mandrel straddling, in their working position, the batting strips of the longitudinal side thereof, which carries the free end 6 of the withdrawing tape 8. The winding mandrel has a bore 14 passing through it longitudinally and is connectable to a vacuum source 15 identified by an arrow. One fork slot 16 of the winding mandrel 11 is cut deeper into the wall of the hollow winding mandrel on a side facing in the direction of movement of the batting trip. In the direction away from the fork end, there is formed an aspiration aperature 17.

The winding mandrel is rotatably and axially displaceably mounted in bushed bearings 18 and 19 of a housing 20, the rear end of the winding mandrel opening into a tubular connection 21 on the housing to which a suction line 22 is connected.

To the winding mandrel there is keyed a pinion 23 whch meshes with a gear 24. The gear 24 is mounted on a shaft 25 of an intermittent drive 26 whose driving shaft 27 carries a V-belt pulley 28 outside of the housing, said pulley being connected by a V-belt 29 to another V-belt pulley 30 which is fastened on the shaft of a driving motor 31.

A cam 95 is also affixed to the driving shaft 27 and its groove 32 is engaged by the roller 33 on a two-armed lever 34 which is pivoted on a shaft 35. A roller 36 located on the opposite end of lever 34 movably engages a notch 37 in a yoke 38 which extends around both ends of the pinion 23 in close engagement therewith. The winding mandrel passes through the yoke with clearance so that it is freely rotatable in relation therewith. The yoke 38 is displaceably carried by a guide block 39 on a guiding rod 40 fastened parallel to the winding mandrel within the housing.

In the position shown in FIG. 2, the winding mandrel 11 is thus in the starting position for the winding operation, wherein it straddles the batting strip 7, the tines of the fork being located over or in the vicinity of the withdrawing tape which is slung about the batting strip and drawn into a loop, and the free end 6 of the withdrawing tape is sucked through the aspiration aperature 17 into the longitudinal bore 14. The batting strip is held in a horizontal outstretched position and can now be wound upon itself by the rotation of the winding mandrel, without any need for consideration of the presence of the withdrawing tape and its free end 6. The winding speed therefore is not dependent upon the behavior of the free end of the withdrawing tape.

Figure 3:
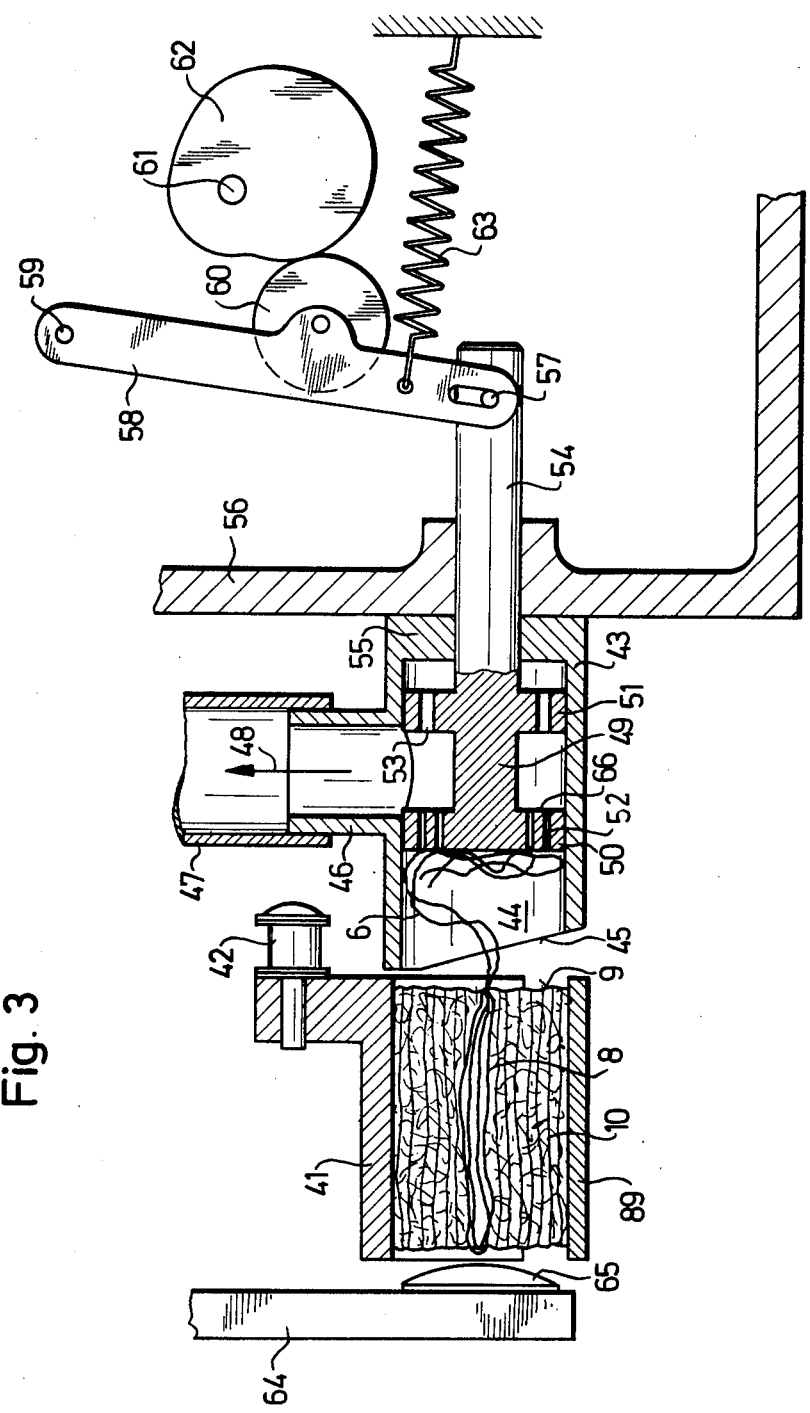
FIG. 3 represents the withdrawing tape application station in a cross-sectional view taken along line III—III of FIG. 1, in the position of aspiration.

In the winding operation the ends of the fiber batting strip 7 may be drawn into the winding cup 41 and there they can be applied to the roll, as will be described further on. Such a winding cup may be wholly or partially a component of a conveyor chain 42 by means of the roll may be carried to the withdrawing tape application station shown in FIG. 3. In FIG. 3 the winding cup 41 assumes a momentary position coaxial to a cylinder housing 43, the side 9 of roll 10 which carries the free end of the withdrawing tape being located on the side facing the withdrawing tape application station. The withdrawing tape application station consists of a cylinder housing 43 whose cylinder orifice 44 is coaxially opposite the roll. The approximately perpendicular margin of the orifice of the cylinder slants downwardly away from the roll towards the free end of the withdrawing tape, so that the free end 6, which at first is hanging down from the roll, can easily be sucked into the cylinder housing.

For this purpose the cylinder housing is provided at approximately the middle of its length with a connection 46 to which a line 47 is connected which leads to a vacuum source, which is not shown, as indicated by the arrow 48. In the cylinder housing 43 there is displaceably mounted a sliding piston 49 consisting of a pressing head 50 and a guiding and pressure-relieving head 51 is connected therewith and spaced axially therefrom. The pressing head 50 is provided through bores 52 of relatively small diameter, while the pressure-relieving head 51 has passages 53 of greater diameter in comparison. The clear distance between the two heads 50 and 51 corresponds approximately to the inside diameter of the connection 46. The connecting rod 54 of the sliding piston 49 passes through a cylinder head 55 and a housing wall 56 and its extremity is connected by a pin-and-slot joint 57 to a lever 58 which can pivot about a pivot point 59. On the lever 58 there is rotatably mounted a roller 60 which follows a cam 62 rotatable about a shaft 61. A tension spring 63 provides for constant application of the cam follower 60 to the cam.

On the side of winding cup 41 facing away from the cylinder housing 43 there is provided a block 64 which is provided in the area of the orifice of winding cup 41 with a convex contact surface 65.

In the operating position shown in FIG. 3, the sliding piston 49 is in the final position of its back stroke in which the two piston heads 50 and 51 are astride the orifice of the vacuum connection 46. The vacuum source is turned on, so that the free end 6 of the withdrawing tape 8 has been aspirated through the downwardly flaring interstice between the orifice of the cylinder housing and the winding cup 41 and against the face of piston head 50. The small bores 52 in piston head 50 provide not only for a certain throttling of the vacuum but also for a random arrangement of the free end of the tape against the face of the piston head.

In FIG. 4 is shown the final position of the working stroke of the sliding piston, in which the latter presses the free end 6 of the withdrawing tape in the described random arrangement against the end of the roll 10, piston head 50 entering into the winding cup 41 so that the roll 10 contacts at its other end the convex contact surface 65 and a secure adhesion of the free end of the withdrawing tape to the end of the roll is assured. This is achieved by the fact that, as a result of the random arrangement, numerous sections of the free end of the withdrawing tape lie against the tampon batting material of the roll, the fiber material of the free withdrawn tape intermeshing partially with that of the roll such that a secure adhesion of the end of the tape to the end of the roll after the pressing process is assured. The roll, which in FIG. 4 has been compressed axially, resumes approximately its original length after the return of piston head 50.

The rear edge 66 of piston head 50, in the instant in which the folded tape ends encounter the end 9 of roll 10, leaves the housing cylinder 43, so that air now passes from without through the larger 53 of the pressure relief head 51. The suction is therefore no longer acting on the face of the pressing piston head, and the aspiration of filaments or the raising of fuzz is prevented.

The random arrangement of the free end 6 of the withdrawing tape is represented more clearly in FIG. 6, in which it extends over the entire end surface 9 of the roll 10, which is now ready for pressing and which upon the next advancint step of chain 42 will more in the roll cup 41 to a station where it will be transferred to another chain system and will then move on to a pressing station as will now be described.

Figure 1:
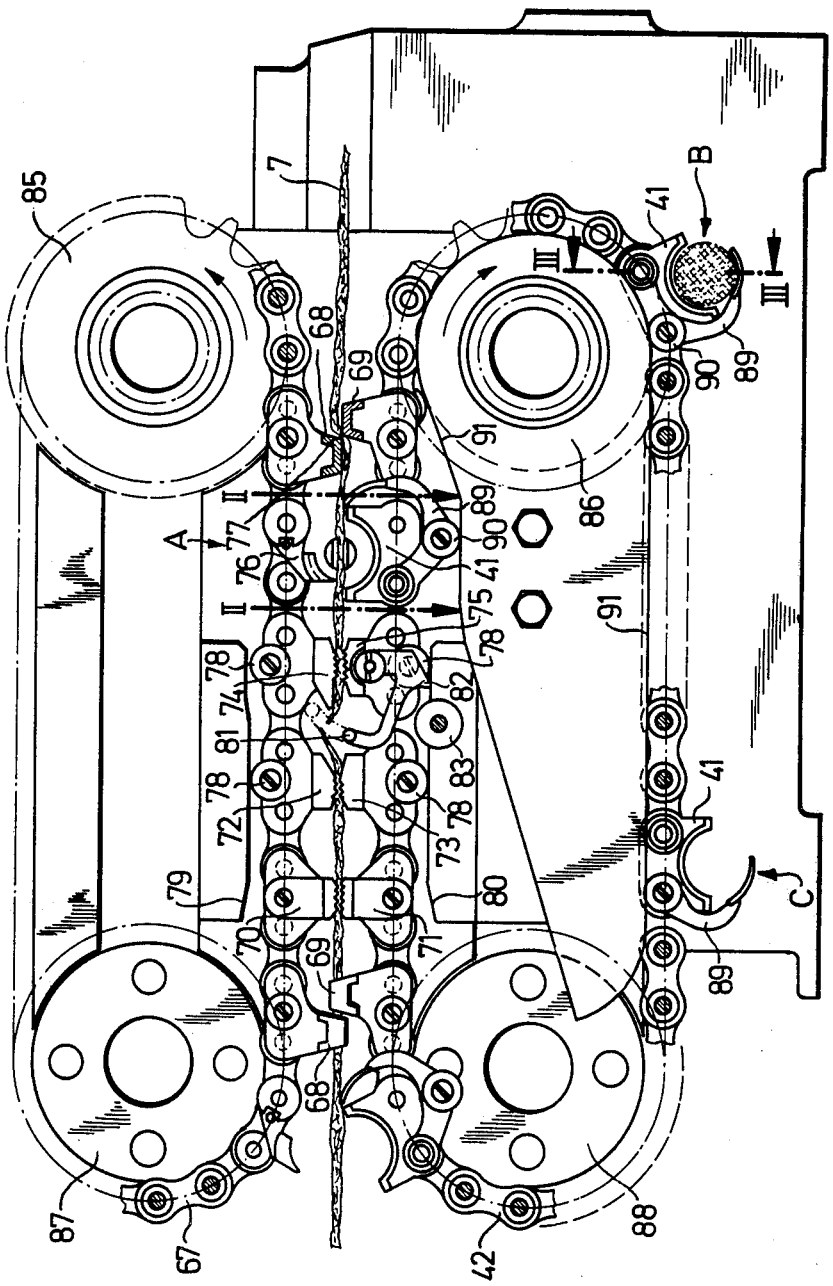
FIG. 1 is a front elevational view of the apparatus with the rolling station, the withdrawing band application station and the ejection station.

In FIG. 1 there is represented an apparatus in which the above-described winding station is at A, the withdrawing tape application station is at B, and a transfer station leading to a tampon press is indicated at C. This systems, with which extraordinarily high operating speeds may be achieved, consists of the lower conveyor chain 42 shown in FIGS. 3 and 4 and also of an additional endless upper conveyor chain 67, these chains being driven step-wise in synchronism in a common perpendicular plane of rotation, one clockwise and the other counterclockwise as indicated. In the position represented in FIG. 1, in which the roll 10 is located in the application station B with the conveyor chains stopped and the winding mandrel 11 is just beginning the winding process, the interacting sections of the two conveyor chains 42 and 67 have attached to them, from left to right in the figure, the cooperating tension jaws 68—69, and three successive pairs of gripping jaws 60–71, 72–73 and 74–75. The last pair of adjoined by a winding cup 41 on chain 42 with a wiping arm 76 disposed above it on chain 67. Winding cup 41 is then followed by another pair of tension jaws 68–69.

The associated tension jaws 68–69 are offset from one another such that the batting strip 7 is slightly kinked when these jaws are in the engaged position, as shown at 77 in the right pair of tension jaws. These tension jaws are provided on both sides with raised margins serving for the precise guidance of the batting strip. On the other hand, the gripping jaw pair 70–71 consists of elements whose engaging surfaces are opposite one another and are provided with teeth or grooves to improve their gripping action. The gripping jaws of the next two pairs are each provided with a roller 78, these rollers running onto cam rails 79–80 in the area where the section of batting is severed, so that in this area of the apparatus the jaws of these two pairs will be forced tighter together so as to grip the batting strip more tightly. The upper cam rail 79 is supported yieldingly, by means of a spring which is not shown, on a beam which is fastened to a wall of the structure. In like manner the lower cam rail is supported on a beam fastened to a wall of the housing.

A severing bail 81 is additionally pivoted on gripping jaw 75, and its relatively blunt arm extends over the width of the batting strip 7. On this severing bail there is provided a slanting surface 82 which during the forward movement of the conveyor chains runs up upon a roller 83 mounted on the lower cam rail 80. In this manner the severing bail is swung transversely of the batting strip to the position indicated by the broken lines, in which the adjacent pairs of gripping jaws are forced together by the cam rails. In this manner the fibers of the batting strip are pulled apart and substantially separated by means of the severing bail. In the position represented in FIG. 1, this procedure has just been completed, so that the rollers 78 of the pair of gripping jaws 74–75 have already been released again by the cam rails, so that the winding mandrel can easily pull the piece of batting out of this pair of gripping jaws.

While the conveyor chains stopped, the winding mandrel is pushed forward by the control cam 95 (FIG. 2) substantially concentrically with the approximately semicircular winding cup 41, and with its upper and lower fork tines straddles the batting strip. Thereupon the intermittent drive 26 starts the rotatory movement of the winding mandrel, so that the severed section of batting is wound up approximately from its center. The winding cup 41 cooperates with a wiping arm 76 on the upper chain 67, which extends over the width of the batting strip and applies itself with adjustable spring force against the batting material so that the desired outside diameter of the roll is achieved. The pair of tension jaws 68–69 which is disposed after the winding cup 41 serves in this operating position mainly for the purpose of kinking the batting strip to exercise a certain tension on the one end of the severed section of batting so as to counteract the tension resulting from the complete parting of the substantially separated fibers at the point of severance.

After completion of the winding process and the withdrawal of the winding mandrel 11, the roll 10 at first continues to be held in the winding cup 41 by the wiping arm 76 during the following transporting movement of the conveyor chain passing around the sprockets 87 and 88. As the circulatory movement of the conveyor chains continues, the wiping arm is lifted so that the roll would lie free in the winding cup 41 and would fall out as it passed around the drive sprocket 86. To prevent this a curved lever 89 is articulated to the winding cup and is pivoted by means of a cam follower 90 running on a cam 91 in such a manner that the free end of the lever, which is bent to fit the roll diameter, combines with the winding cup 41 to form a more or less closed transport chamber for the roll, as illustrated at the withdrawing tape application station B.

The distance between the winding cups and between the pairs of tension jaws corresponds to the length of the section of batting which is to be severed, and the distance between the sprockets of the conveyor chains is of the same order of magnitude. This brings it about that, when a wound roll is put out, another section of batting will already be located in the winding system, thereby eliminating waste motion. In like manner, there are on the conveyor chains a total of four sets of the elements mounted on the links of the chains.

The cylinder housing 43 of the withdrawing tape application station shown in FIG. 3 is thus coaxial with the winding cup 41 in the area of the lower section of conveyor chain 42 and of cam 91 whose cam surface extends approximately over the entire area in which the lower conveyor chain 42 moves from its roll processing section to its bottom section, as well as along the bottom section beyond a roll transfer station C formed by an ejector plunger, which is not shown, to a point beyond which the lower conveyor chain passes around sprocket 88 to re-enter the roll processing section.

It is thus apparent that, by means of the described apparatus, the free end 6 of the withdrawing tape can be brought into a position extending away from the batting strip 7 by means of the hollow winding material prior to the winding of said batting strip, before the free end of the withdrawing tape, after another advancing step of the conveyor chains 42 and 67, is pressed in a random state against the end 9 of the roll 10 so as to adhere thereto at the withdrawing tape application station.

We claim:

1. In an apparatus for winding a batting strip into a tampon batting roll wherein one end of a withdrawing tape is joined to said batting strip and the other end of said tape is free, and wherein said apparatus comprises a rotatable, forked winding mandrel having fork tines, said mandrel adapted to be positioned adjacent to the longitudinal side of said batting strip which bears the free end of the withdrawing tape with said fork tines straddling said longitudinal side whereby said strip is wound into said roll by rotating said mandrel about an axis perpendicular to said longitudinal side of said strip, the improvement wherein said mandrel is provided with an axial bore therethrough having a first open end adapted to be positioned adjacent to said longitudinal side and a second open end in flow communication with a source of vacuum whereby said free end of said withdrawing tape may be aspirated into said bore when winding said strip.

2. The apparatus of claim 1 wherein the fork tines are defined by first and second slots cut through the mandrel wall and extending axially from one end of the mandrel partially toward the other end, said first slot having a terminal closer to said other end of the mandrel than said second slot whereby when said fork tines straddle said longitudinal side of said strip, said longitudinal side will bear against the terminal of the second slot and be displaced from the terminal of the first slot, said displacement defining an aperture for aspirating the withdrawing tape into the mandrel bore.

3. An apparatus for applying the free end of a withdawing tape to one end of a tampon batting roll, said withdrawing tape having its other end joined to said batting roll, said apparatus comprising:

a cylinder having a bore therethrough with one end open and adapted to be positioned adjacent to said one end of said tampon batting roll with said bore coaxially aligned with said batting roll;

a piston, slidably disposed within said cylinder bore, said piston having a plurality of apertures therethrough;

means for drawing air from said one end of said bore through said aperture whereby said withdrawing tape may be aspirated into said bore and against said apertures; and means for urging said piston against said one end of said batting roll to dispose said withdrawing tape thereon in a random pattern.

4. The apparatus of claim 3 wherein the axis of the cylinder lies in a substantially horizontal plane and the open end of said bore slants downwardly and away from said one end of said tampon batting roll to facilitate the aspirating of withdrawing tape into said bore.

5. The apparatus of claim 3 wherein means are provided for positioning and retaining said one end of said tampon batting roll into coaxial alignment with said cylinder, said means comprising a cylindrical, hollow open ended winding cup having an inside diameter larger than that of said piston.

* * * * *